US010827963B2

(12) United States Patent
Sink et al.

(10) Patent No.: US 10,827,963 B2
(45) Date of Patent: Nov. 10, 2020

(54) APPARATUS FOR RAPID COLLECTION OF BLOOD FROM LIVESTOCK

(71) Applicant: Advanced Animal Diagnostics, Inc., Morrisville, NC (US)

(72) Inventors: John Richard Sink, Raleigh, NC (US); Jasper N. Pollard, Durham, NC (US); Gustavo Pena, Canyon, TX (US); Deborah Asion, Durham, NC (US); Mitchell Hockett, Raleigh, NC (US); Joy Parr Drach, Pontiac, IL (US); Martha Payne, Hillsborough, NC (US); David A. Calderwood, Chapel Hill, NC (US)

(73) Assignee: Advanced Animal Diagnostics, Inc., Morrisville, NC (US)

( * ) Notice: Subject to any disclaimer, the term of this patent is extended or adjusted under 35 U.S.C. 154(b) by 245 days.

(21) Appl. No.: 15/882,621

(22) Filed: Jan. 29, 2018

(65) Prior Publication Data

US 2018/0228417 A1 Aug. 16, 2018

Related U.S. Application Data

(63) Continuation-in-part of application No. PCT/US2016/044210, filed on Jul. 16, 2016.
(Continued)

(51) Int. Cl.
*A61B 5/00* (2006.01)
*A61B 5/15* (2006.01)
(Continued)

(52) U.S. Cl.
CPC .... *A61B 5/150061* (2013.01); *A61B 5/15003* (2013.01); *A61B 5/150022* (2013.01);
(Continued)

(58) Field of Classification Search
CPC ............... A61M 5/343; A61B 5/15003; A61B 5/150022; A61B 5/150061;
(Continued)

(56) References Cited

U.S. PATENT DOCUMENTS 3,677,448 A * 7/1972 Harris, Sr. .............. B01L 3/022
222/387
3,747,812 A 7/1973 Karman et al.
(Continued)

FOREIGN PATENT DOCUMENTS

DE 4132480 4/1993
EP 0 047 176 3/1982
EP 1 740 096 4/2005

OTHER PUBLICATIONS

Written Opinion and International Search Report for PCT/US2016/044210 dated Oct. 28, 2016, 13 pages.

*Primary Examiner* — Max F Hindenburg
(74) *Attorney, Agent, or Firm* — Myers Bigel, P.A.

(57) ABSTRACT

An apparatus useful for the rapid collection of blood from a subject (e.g., a blood vessel, such as the vein, artery or capillary bed of a bovine subject) and dispensing the blood therefrom into a test or collection device. In general, the apparatus comprises: (a) a body having a chamber formed therein, said chamber having an inlet and outlet, with said chamber configured to draw blood therein; (b) a hollow barrel connected to said chamber outlet; (c) an ejector operatively associated with said barrel; (d) a hollow needle connected to said body, with said hollow needle in fluid communication with said chamber through said inlet, so that blood can be rapidly drawn into said chamber through said needle. The needle is optionally removed and blood dispensed from the body into a test or collection device by actuating the ejector.

25 Claims, 5 Drawing Sheets

Related U.S. Application Data (60) Provisional application No. 62/198,405, filed on Jul. 29, 2015.

(51) Int. Cl.
*A61B 5/153* (2006.01)
*A61M 5/34* (2006.01)
*B01L 3/02* (2006.01)
*A61M 5/31* (2006.01)
*A61M 5/315* (2006.01)

(52) U.S. Cl.
CPC ...... *A61B 5/1535* (2013.01); *A61B 5/150099* (2013.01); *A61B 5/150213* (2013.01); *A61B 5/150221* (2013.01); *A61B 5/150259* (2013.01); *A61B 5/150389* (2013.01); *A61B 5/150503* (2013.01); *A61B 5/150755* (2013.01); *A61M 5/343* (2013.01); *A61B 5/150236* (2013.01); *A61B 2503/40* (2013.01); *A61M 5/31531* (2013.01); *A61M 5/344* (2013.01); *A61M 5/346* (2013.01); *A61M 2005/3128* (2013.01); *B01L 3/0217* (2013.01)

(58) Field of Classification Search
CPC ........ A61B 5/150099; A61B 5/150213; A61B 5/150221; A61B 5/150259; A61B 5/150503; A61B 5/150755; A61B 5/1535
See application file for complete search history.

(56) References Cited

U.S. PATENT DOCUMENTS

| | | | | |
|---|---|---|---|---|
| 3,882,849 | A | * | 5/1975 | Jamshidi ............ A61B 10/0283 600/566 |
| 4,133,304 | A | | 1/1979 | Bailey |
| 4,263,922 | A | | 4/1981 | White |
| 4,576,185 | A | * | 3/1986 | Proud .................. B01L 3/5082 600/573 |
| 4,595,021 | A | | 6/1986 | Shimizu et al. |
| 4,660,569 | A | | 4/1987 | Etherington |
| 4,861,335 | A | * | 8/1989 | Reynolds ............ A61M 5/2448 604/88 |
| 5,147,314 | A | * | 9/1992 | Vaillancourt ...... A61M 25/0111 604/158 |
| 5,147,329 | A | * | 9/1992 | Brannon ............ A61B 5/15003 600/577 |
| 5,919,356 | A | | 7/1999 | Hood |
| 6,524,533 | B1 | | 2/2003 | Tyrrell |
| 8,092,394 | B2 | | 1/2012 | Harman et al. |
| 2003/0023189 | A1 | | 1/2003 | Kuo |
| 2004/0199085 | A1 | | 10/2004 | Young et al. |
| 2005/0054949 | A1 | | 3/2005 | McKinnon et al. |
| 2008/0027385 | A1 | | 1/2008 | Boecker et al. |
| 2008/0312576 | A1 | * | 12/2008 | McKinnon ......... A61B 5/15003 604/6.15 |
| 2010/0015657 | A1 | | 1/2010 | Dlott |
| 2014/0052066 | A1 | | 2/2014 | Dangoisse |

* cited by examiner

SECTION A - A

FIG. 9

APPARATUS FOR RAPID COLLECTION OF BLOOD FROM LIVESTOCK

RELATED APPLICATIONS

This application is a continuation-in-part of International Application No. PCT/US2016/044210, filed Jul. 27, 2016 and published as PCT Publication No. WO/2017/019743, which in turn claims the benefit of U.S. Provisional patent application Ser. No. 62/198,402, filed Jul. 29, 2015, the disclosures of which are incorporated by reference herein in its entirety.

FIELD OF THE INVENTION

The present invention concerns apparatus for rapidly collecting blood from a subject, particularly veterinary subjects such as cattle and other livestock, and rapidly dispensing that blood into a receptacle or directly into a test for further analysis.

BACKGROUND OF THE INVENTION

The world cattle population is estimated to be about 1.3 billion head, with about 30% in Asia, 20% in South America, 15% Africa, 14% in North and South America and 10% in Europe. Cattle inventory in the United States as of January 2015 was estimated at 89.9 million head, living on upwards of 600,000 farms and ranches. Cumulatively, the beef industry has an economic impact of $44 billion.

Approximately 20% of any one feedlot's cattle will become sick with infection. It is difficult to identify which cattle are sick and preventative diagnostic measures are lacking. As a result, cattle considered to be at high risk will typically be treated with antibiotics. To illustrate how widespread this practice has become, a recent report found agriculture accounts for 80% of antibiotic sales. With public concern mounting against the use of antibiotics in livestock, ranchers and farmers are forced to choose between medicating healthy cattle or risking pathogenic exposure to their entire herd.

The cattle chute at the feedyard provides convenient access to individual animals, but the amount of time each animal is available for withdrawal of a blood sample while in the chute is short. Accordingly, development of methods and apparatus for rapid withdrawal of blood from cattle as they pass through the chute, which blood can then be used for individual detection of infection, allowing for treatment on an animal-by-animal (rather than whole-herd) basis, is urgently needed.

SUMMARY OF THE INVENTION

Initially, we attempted to develop apparatus and methods for withdrawal of blood from the animal's ear. These techniques were found to be too slow (albeit by a matter of tens of seconds), and insufficiently reliable. In addition, blood flow to the ear is reduced when the body temperature is lower, making these procedures less reliable in cold weather.

We also proposed methods and apparatus for withdrawal of blood from the animal's snout. Initial testing seemed successful, but the possible risk of infection when the animal is subsequently feeding (with its snout often contacting food shared with other animals) made such techniques unacceptable to some feedlots.

After further efforts, we developed, and herein describe, an apparatus useful for the rapid collection of blood from a subject (e.g., a blood vessel, such as the vein, artery or capillary bed of a bovine subject) and dispensing the blood therefrom into a test or collection device. In general, the apparatus comprises:

(a) a body having a chamber formed therein, said chamber having an inlet and outlet, with said chamber configured to draw blood therein;

(b) a hollow barrel connected to said chamber outlet;

(c) an ejector operatively associated with said barrel;

(d) a hollow needle connected to said body, with said hollow needle in fluid communication with said chamber through said inlet, so that blood can be rapidly drawn into said chamber through said needle. The needle is optionally removed and blood dispensed from the body into a test or collection device by actuating the ejector (e.g., depressing a plunger or compressing a bulb).

The present invention is explained in greater detail in the specification below, which sets for non-limiting examples and embodiments. While the invention is explained primarily with reference to its primary purpose of collecting jugular vein blood from bovines such as cattle, it will be appreciated that the invention can be used on other human or animal subjects (particularly veterinary and livestock subjects such as rabbits, goats, sheep, horses, pigs, etc.) and can be used to collect blood from other locations (e.g., other veins such as the cephalic vein, saphenous vein, ear vein, milk vein (i.e., the subcutaneous abdominal vein), tail vein (i.e., the coccygeal vein), median cubital vein, etc, as well as blood from capillary beds and arteries).

DETAILED DESCRIPTION OF ILLUSTRATIVE EMBODIMENTS

The present invention now will be described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

FIGS. 1-4 show a non-limiting example of present invention. As noted above, the apparatus comprises, in overview, a collection and dispensing subassembly 10, a connecting hub 30, and a hollow needle 40.

The collection and dispensing subassembly generally includes a body 11 having a chamber 12 formed therein, the chamber having an inlet 13 and outlet 14, with the chamber configured to draw blood therein through the inlet. A hollow barrel 21 is connected to the capillary chamber outlet, a hollow barrel connected to the chamber outlet. The barrel has a barrel chamber 22, and an ejector or plunger 25 is positioned in the barrel.

The hollow needle 40 is in some embodiments removably connected to the body 11, with the hollow needle in fluid communication with the chamber 12 through the inlet 13, so that blood can be rapidly drawn into the chamber 12 through the needle 40.

In some embodiments, the body 11 is a capillary body and the chamber 12 is a capillary chamber that are sized and configured such that capillary action may be used to draw blood more rapidly into the chamber 12. However, in some embodiments, the pressure of a blood vessel (vein, or artery, or capillary bed) may be sufficient to draw blood into the chamber 12 (when present) with or without significant contributions from capillary action in the chamber 12. Thus, in some embodiments, the chamber 12 may be sized (e.g., larger than a typical capillary blood collection tube) such the chamber 12 is filled primarily by pressure without significant contributions from capillary action. In particular embodiments, however, the capillary action in the chamber 12 may be the primary force to draw blood into the chamber 12.

In some embodiments, an actuator, such as the ejector or plunger 25, may also be used to apply negative pressure to further draw blood into the chamber 12 for rapid collection. As illustrated in FIG. 6-9, the plunger 25 may be omitted, and the ejector may be provided by a bulb 125. As shown in FIGS. 6-9, the apparatus comprises a collection and dispensing subassembly 110, a connecting hub 130, and a hollow needle 140. The collection and dispensing subassembly 110 generally includes a body 111 having a chamber 122 formed therein, the chamber 122 having a first portion with an inlet 113 and outlet 114, such that the chamber 122 is configured to draw blood therein through the inlet 133. A hollow barrel 121 is connected to the chamber outlet 114, a hollow barrel connected to the chamber outlet 114. The bulb 125 is positioned in the barrel 121. In this configuration, the bulb 125 may be compressed and released to create a negative pressure to thereby further draw blood into the chamber 122. It should be understood that the chamber 122 may optionally be a capillary chamber to further assist in the rapid filling of the chamber 122. In some embodiments, some portion of the chamber 122 may be a capillary chamber or tube. For example, the portion of the chamber 122 between the inlet 113 and the outlet 114 may be a capillary tube, the portion of the chamber 122 that is in the barrel 121 may have reduced or negligible capillary action therein. In some embodiments, the chambers 122 may be combined into a single chamber that may or may not be sized for capillary action to assist in filling the chamber 122. With reference to FIGS. 1-4 and 6-9, it should be understood that the bulb 125 of FIGS. 6-9 may be used with the configuration of FIGS. 1-4 or the plunger 25 may be used with the configuration of FIGS. 6-9.

With reference to FIGS. 1-9, the needle may be removed, and then blood is dispensed into a test device or container (not shown) through the inlet 13, 113 by depressing the plunger 25 (FIGS. 1-4) or compressing the bulb 125 (FIGS. 6-9). In other embodiments, the hollow needle 40, 140 may be permanently affixed to (e.g., welded to, thermally bonded to, adhesively connected to, etc.) the body 11, 111.

As shown in FIGS. 1-4, there is optionally a vent opening 26 formed in either the barrel or the plunger 25 (or bulb 125, when a bulb is used in place of a plunger as in FIGS. 6-9), with the capillary chamber 122 in fluid communication with the vent opening 26, to facilitate flow into the chamber 122. In a particularly preferred embodiment, the vent opening is formed in the plunger end portion, or similarly configured on a squeezable bulb, so that it can be covered and blocked by the user's thumb or other digit when the blood is ejected when the plunger is depressed or ejector is actuated. In the bulb 125 of FIGS. 6-9, no vent may be preferred for relatively low blood vessel pressure, and can also be used for relatively high blood pressure, for example, if the bulb 125 is pre-squeezed or compressed prior to inserting or "sticking" the animal with the needle 140.

Preferably, the barrel has at least one laterally projecting grasping projection 27 connected thereto, to facilitate handling by a human user attempting to draw a blood sample from a (sometimes large) animal.

Preferably, the plunger has a blunt end portion 28 configured for depression of the plunger into the barrel by the user, and wherein the vent opening is formed in the blunt end portion (e.g., to facilitate one-handed operation during dispensing, as discussed below).

The chamber, the barrel, the plunger or ejector, and the needle may all be axially aligned with one another to facilitate handling, the other geometries may also be employed (e.g., angled geometries).

The apparatus illustrated further comprises a connecting hub 30 (FIGS. 1-4) and hub 130 (FIGS. 6-9), with both the hollow needle and the body connected to the hub member, and with at least one of the hollow needle and the body removably connected to the hub member. Numerous alternate configurations of the hub member can be implemented, as discussed further below. In the illustrated embodiment, both the capillary body and the hollow needle are removably connected to the hub member, the one with linear frictional engagement, and the other by frictional engagement (or optionally twisting frictional engagement) aided by the Luer lock fitting as discussed below.

Preferably at least a portion of the body is transparent, and the apparatus may include a porous indicator element 15 (e.g., a cotton, synthetic fiber, or glass fiber filter) positioned in the capillary chamber outlet opening adjacent a transparent portion of the capillary body. During use, when the indicator element shows at least partial saturation with blood, the operator knows that the chamber 12 has been sufficiently filled and may withdraw the device from the animal.

In some embodiments, the chamber 12 (FIGS. 1-4) and 122 (FIGS. 6-9) is a capillary chamber and has a volume of from 2.0, 5.0, 10, 20 microliters to 50, 100, 150 or 200 microliters. In some specific embodiments, the chamber has a volume of 20 microliters. In other embodiments, the capillary chamber has a volume of 50 or 100 microliters to 200, 500, or 1000 microliters, or more. The capillary chamber may optionally have an internal diameter and length sized to facilitate capillary or pressure filling of the chamber, such as an internal diameter of about 0.25 mm to about 6.00 mm.

In some embodiments, particularly those suitable for larger animals, the hollow needle 40 has a length of from 5 or 15 millimeters to 30 or 50 millimeters (preferably 25 millimeters), and/or the hollow needle is between 8, 10, 12, 14 or 16 gauge and 20, 22 or 25 gauge (preferably 18 gauge), typically for correspondingly large to small animals. Thus, the needle may be about 25 gauge or smaller. In some embodiments, the hollow needle 40 has at least one lateral vent (e.g., holes, slots, etc., not shown) formed therein and configured to facilitate rapid blood collection.

In the illustrated embodiment, the body and the hollow needle are removably connected to one another through linear frictional engagement, optionally through the hub member 30. In other embodiments, the capillary body and the hollow needle are permanently affixed to one another.

Such a hub member 30 member may comprise at least one laterally projecting grasping member 31 connected thereto, preferably positioned in opposing relation to the grasping member 27 on the barrel, to facilitate rapid removal of the needle from the capillary body.

The chamber may contain a reagent composition in liquid (generally aqueous, including gels) or dry form, such as anticoagulants, chelating agents, stains, dyes, etc.

In some embodiments, an anticoagulant or chelating agent (e.g., a salt of ethylenediaminetetraacetic acid (EDTA) in dry powder form) or droplets of anticoagulant or chelating agent is contained in the chamber 13 in a predetermined amount: That is, an amount appropriate for subsequent diagnostic testing, based on the volume of the capillary chamber, with larger amounts being included when the capillary chamber is large, and smaller amounts included when the capillary chamber is small. Specific amounts are known or readily determined by those skilled in the art based on the particular test being performed and testing apparatus being used. In those embodiments where the needle is not removable, an anticoagulant may be included inside the needle to treat blood which does not progress up into the capillary chamber where the bulk of the anticoagulant resides.

Any suitable anticoagulant or chelating agent may be used, preferably in dry or dry particulate form. In some embodiments of the invention, the one or more anti-coagulants may be abciximab (ReoPro), acenocoumarol, antithrombin III, argatroban, aspirin, bivalirudin (Angiomax), clopidogrel, dabigatran, dabigatran etexilate (Pradaxa/Pradax), desirudin (Revasc/Iprivask), dipyridamole, eptifibatide (Integrilin), fondaparinux, heparin, hirudin, idraparinux, lepirudin (Refludan), low molecular weight heparin, melagatran, phenindione, phenprocoumon, ticlopidine, tirofiban (Aggrastat), warfarin, ximelagatran, ximelagatran (Exanta/Exarta), or any combination thereof. See e.g. U.S. Pat. No. 9,085,615.

In particular embodiments of the invention, the one or more anti-coagulants may be chelators of di-valent cations selected from Ethylenediaminetetraacetic acid (EDTA), Ethylene glycol tetraacetic acid (EGTA), FURA-2, or a combination thereof, particularly dry particulate salts thereof.

In some embodiments, the amount of anti-coagulant in the chamber may be selected and dispersed within the chamber based on the blood volume in the chamber so that a suitable concentration of anti-coagulant in the blood is achieved. In some embodiments, the needle may have a suitable anti-coagulant amount similarly dispersed therein especially if the needle is not removed before dispensing blood. In use, a small amount of blood will collect in the needle, and if the blood in the needle were not exposed to the anti-coagulant, then insufficient blood/anti-coagulant mixing may occur if the blood is ejected through the needle. However, in some embodiments, the anti-coagulant may be omitted from the needle and the needle is preferably removed during the ejection of the blood from the chamber. If the needle is removable, then the needle may be removed and the blood/anti-coagulant may be ejected from the device as described herein without using additional anti-coagulant in the needle and maintaining proper blood/anti-coagulant mixing. An alternative method permits leaving the needle in place with two steps for dispensing: The first step is to purge blood from the needle that may not have been able to mix with anticoagulant. The second step is a further dispense of blood with has mixed with anticoagulant.

In the example embodiment of FIG. 1-4, a suitable barrel and capillary body subassembly, including plunger and indicator plug, is a MINIVETTE® POCT 20 microliter capillary blood collection device, containing a defined or predetermined amount of EDTA tripotassium salt, Reference number 17.2113.120, available from Sarstedt Aktiengesellschaft & Co. A suitable hollow needle is a BD PRECISIONGLIDE™ 18 G×1 (1.2 mm×25 mm) single use needle, Reference number 305195, available from Becton, Dickinson and Company. A suitable hub member is formed from an EXEUNT® 1 milliliter Luer lock tip disposable syringe, reference number 26050, available from EXEL International, with the plunger discarded and the upper portion of the barrel cut off, leaving the lower portion of the barrel 32 to guide insertion of the capillary body 12 during assembly. Note that the foregoing includes a Luer lock fitting 31, which both cooperates in receiving the corresponding Luer lock fitting fitting 41 on the needle, and which conveniently forms the projecting/grasping element (in this case an annular grasping element) described above.

Those skilled in the art will appreciate numerous variations to the foregoing. For example, the hub member 31 can be a custom-molded part, rather than cut from a syringe body. One or more projecting members on the hub can be enlarged and shaped to be more readily grasped by a user, rather than fortuitously formed from the angled exterior intersection of the syringe barrel and the Luer lock tip thereon. The hub can be permanently connected to the hypodermic needle, or can be permanently affixed to or formed on, the blood collection subassembly 10 (which can itself be a custom-made part, to facilitate connection to the hollow needle, and optionally the removable hub).

In addition, while the example embodiment of FIGS. 1-4 has two removable connections (the first a Luer lock connection of the needle to the hub via corresponding Luer lock fittings 31,41; the second the linear frictional connection of the 30 hub to the capillary blood collection device 10), when a single removable connection is employed it is preferably a linear frictional connection to facilitate rapid removal of the needle from the capillary collection subassembly (although, in a still further embodiment, projecting "wings" can be formed on the hub and/or capillary collection subassembly, to facilitate separation of the two by rapid twisting by the user).

Figure 1:
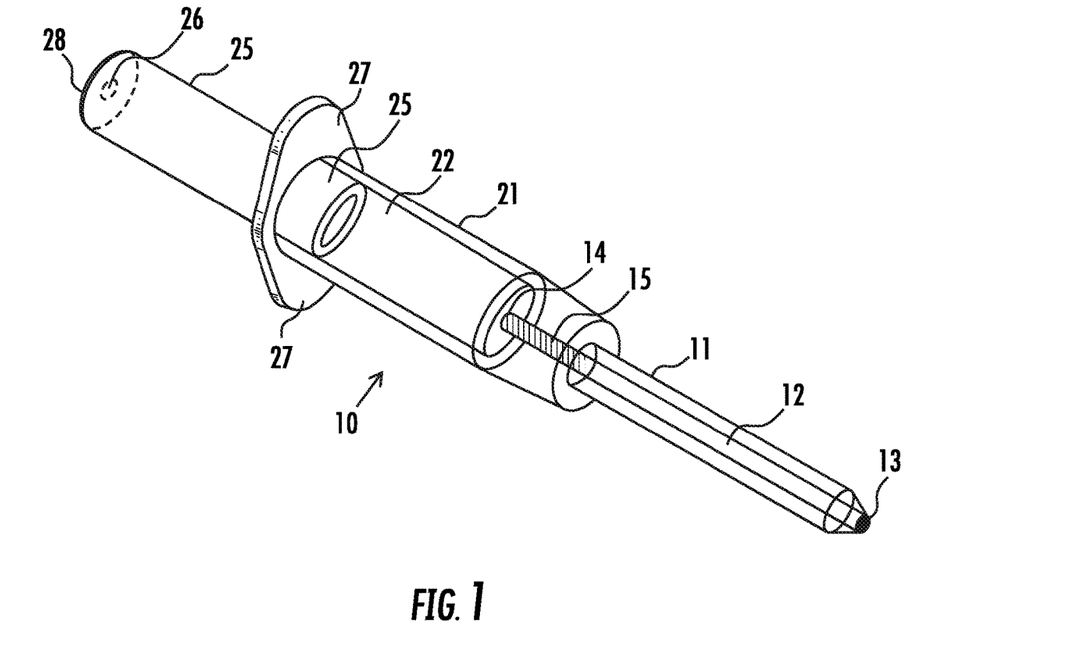
FIG. 1 is perspective view of an example pipette and plunger sub-assembly for use in carrying out the present invention.
Figure 2:
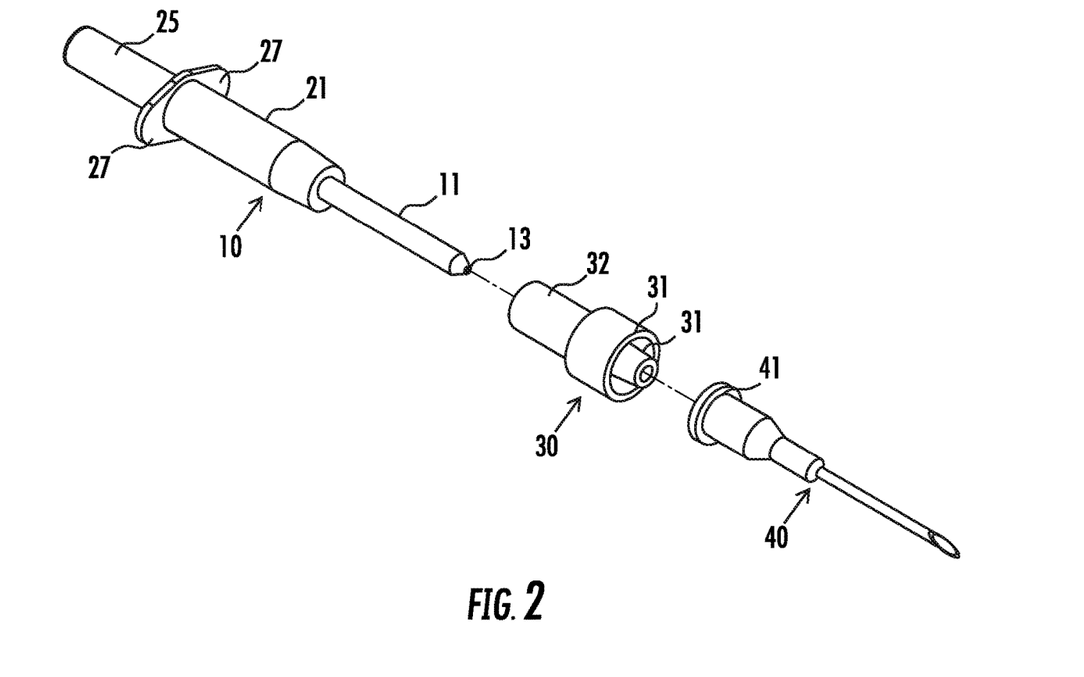
FIG. 2 is an exploded perspective view of a pipette, connector, and needle assembly of an example embodiment of the present invention.
Figure 3:
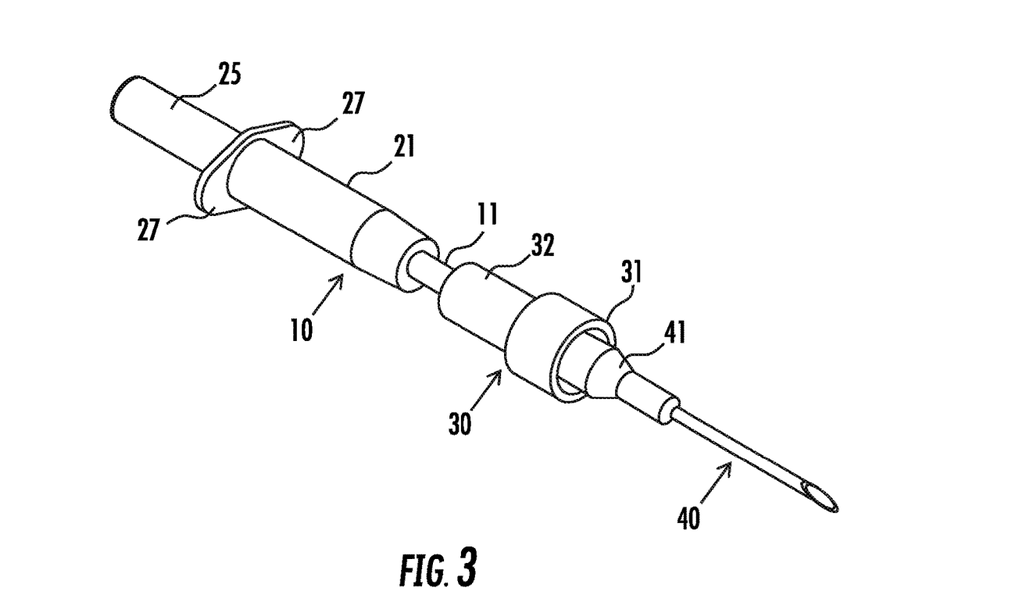
FIG. 3 is a perspective view of the combination of FIG. 2, with the separate components assembled together, and ready for use in collecting blood from the jugular vein of a cow.
Figure 4:
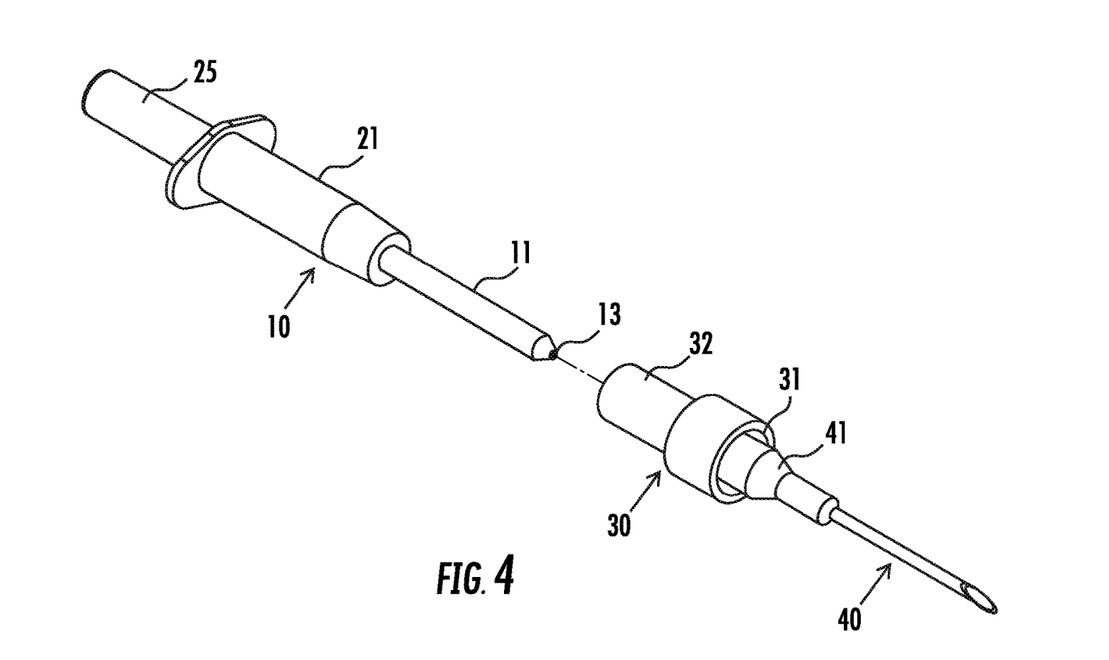
FIG. 4 is a perspective view of the combination of FIG. 3, with the needle and connector hub removed, so that blood can be rapidly dispensed from the pipette and plunger subassembly into a blood sample receptacle for further analysis.
Figure 5:
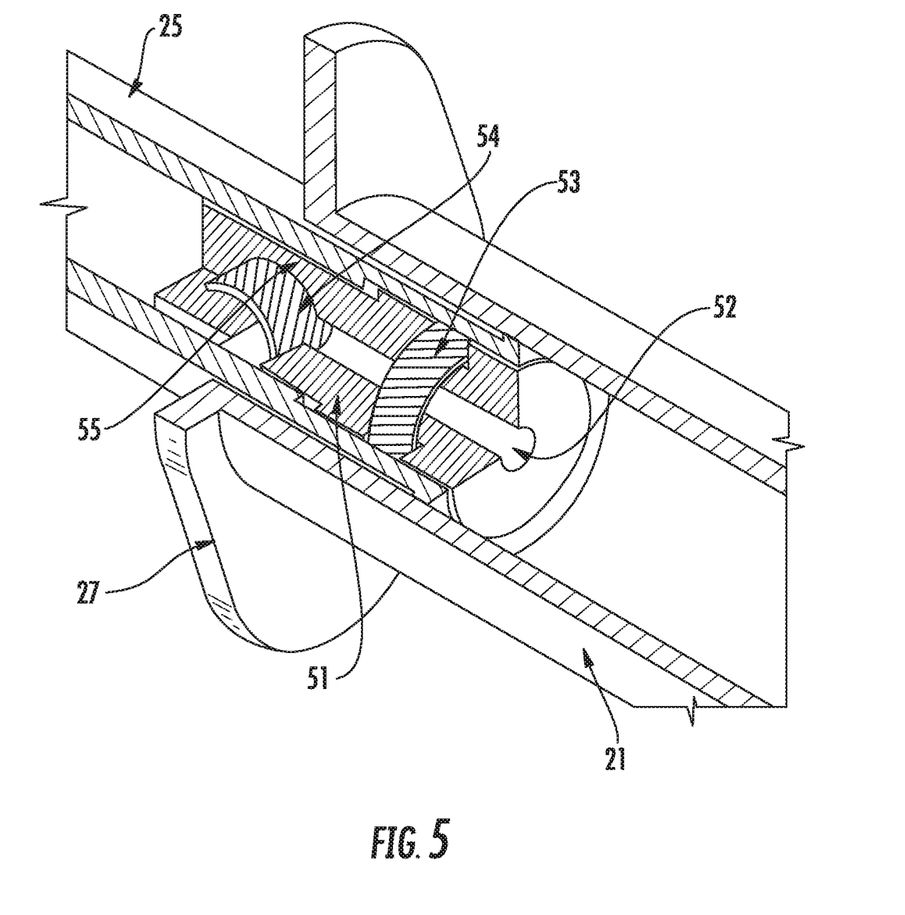
FIG. 5 is a perspective view of one embodiment of a one way valve, or check valve, positioned in a device of FIGS. 2-4.
Figure 6:
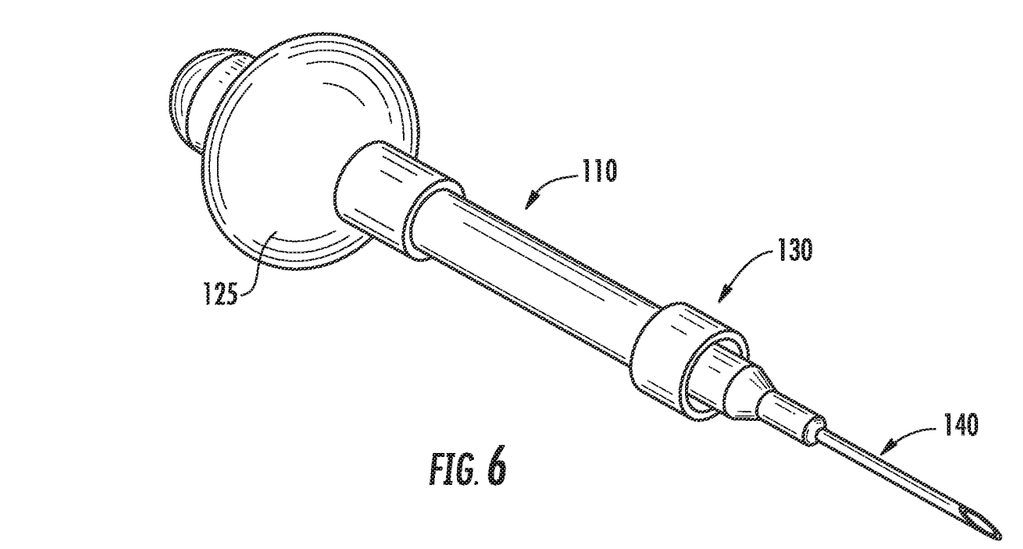
FIG. 6 is a perspective view of another example of a pipette, connector, needle assembly and ejector bulb of an example embodiment of the present invention.
Figure 7:
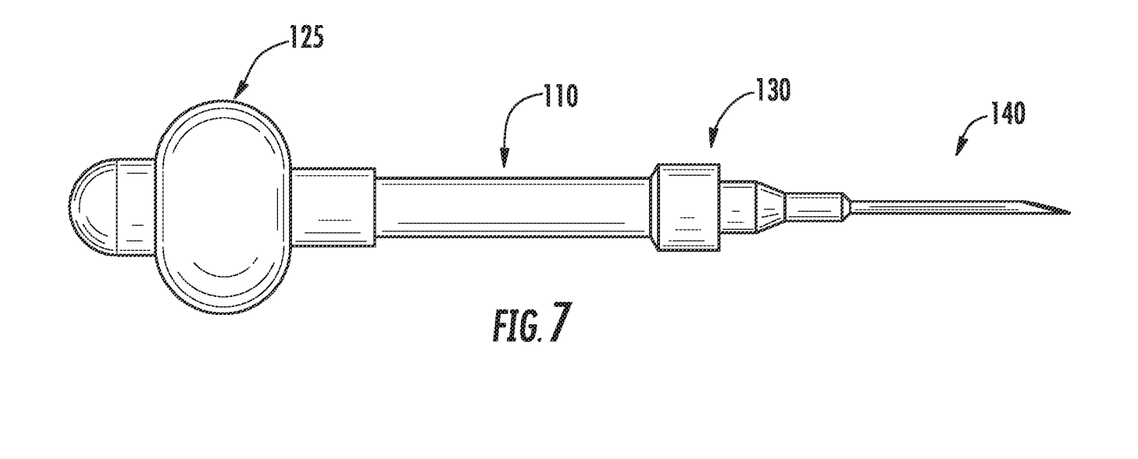
FIG. 7 is a side view of the device of FIG. 6.
Figure 8:
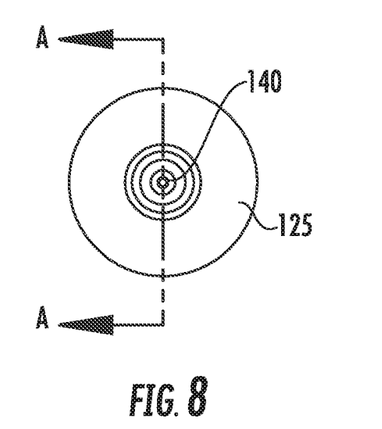
FIG. 8 is a front view of the device of FIGS. 6-7.
Figure 9:
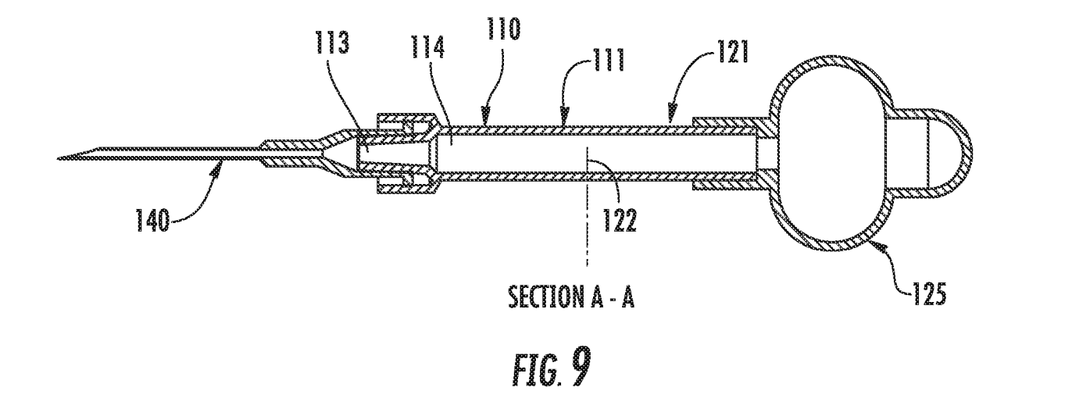
FIG. 9 is a cross sectional view along lines A-A of FIG. 8.

FIG. 5 illustrates one embodiment of a device of the invention incorporating a one-way valve, or check valve. The purpose of the check valve is to inhibit the back-flow of collected blood from the device back into the animal, particularly when the device contains liquid or dry reagents in the capillary chamber for mixing with the collected blood. In the illustrated embodiment, the check valve comprises a valve body 51 inserted into the hollow plunger 25. The valve body may be formed of any suitable material, such as polymer injection molded or fabricated by additive manufacturing. The valve body includes a vent opening 52, and may include an O-ring seal 53 (or other suitable sealing features) to seal the valve body to the interior wall of the hollow plunger. The valve itself may be a flapper valve 54, as illustrated, formed from any suitable material, such as glove latex or a sheet of silicone rubber, which in the illustrated embodiment is affixed into the valve body 51 in a valve body retaining portion 55, which valve body retaining portion is configured to geometrically retain the flapper valve in the valve body without the need for adhesive or other fastener. Numerous alternatives for the position of the check valve are available, including above the vent opening 28, within the plunger 25, as shown, within barrel chamber 22 (so long as sufficient clearance for the plunger is provided), between barrel chamber 22 and capillary chamber 12, between capillary chamber 12 and hollow needle 40, etc. (though in some of these embodiments, the check valve would preferably be configured to overcome by relatively high plunger pressure to expel blood).

In preferred embodiments, the check valve is positioned on the "gas side" or "vent side" above, or upstream from, the barrel chamber (i.e., above the vent opening or within the plunger, or between the barrel and a squeezable bulb). Methods of use. Devices as described above may be used to collect blood from a subject by:

(a) inserting the hollow needle of an apparatus as described above (see, e.g., FIG. 3) into the subject for a time sufficient for said capillary chamber to at least partially fill with said blood sample;

(b) withdrawing the needle from the subject;

(c) optionally separating the needle from the capillary chamber (see, e.g., FIG. 4); and then (d) dispensing the blood sample from the capillary chamber into a collection device (e.g., from the capillary chamber, or through the needle when the needle is not separated from the chamber) by depressing said plunger, squeezing the bulb, or otherwise actuating the ejector.

In some embodiments, the subject is a bovine (including bulls, steers, cows, and calves), although the method may be applied to other subjects as noted above.

In some embodiments, the needle is inserted into a vein (e.g., the jugular vein) of the subject, although other locations may sometimes be used as well, particularly tissues rich in capillary beds, arteries or other blood vessels.

In some embodiments, the procedure is carried out rapidly, for example, with steps (a) through (d) are being carried out in a time of one minute or less, or even thirty or twenty seconds or less (e.g., an average time of one minute, or thirty or twenty seconds, or less, when blood is collected sequentially from two or more subjects). When time is not a major concern, the procedure may be carried out more slowly.

Dispensing of the blood sample may be into any suitable collection device or receptacle for further analysis. Numerous alternatives are known in the art, with particular examples including, but not limited to, those described in U.S. Pat. No. 9,023,641, and in US Patent Application Publication Nos. 2014/0315242, 2014/0315283, and 2014/0186859, the disclosures of which are incorporated by reference herein in their entirety.

While the invention has been described above with a push-type plunger, note that the plunger can be used as a push-pull type plunger, which would facilitate blood collection from certain sources such as a tail vein, e.g., by use of negative pressure. For such a use, additional elements (e.g., rings, tabs, etc.) can be added to the plunger to facilitate pulling by the user. A pre-squeezed or compressed bulb can also be used to create negative pressure.

In addition, while the invention has been described above with a rigid capillary portion, the capillary portion may alternatively be formed of a flexible material, for example, to facilitate ejection of the blood sample by squeezing the capillary portion.

The foregoing is illustrative of the present invention, and is not to be construed as limiting thereof. The invention is defined by the following claims, with equivalents of the claims to be included therein.

That which is claimed is:

1. An apparatus useful for the rapid collection of blood from the blood vessel of a subject and dispensing the blood therefrom, the apparatus comprising:
   (a) a body having a chamber formed therein, said chamber having an inlet and outlet, with said chamber configured to draw blood therein;
   (b) a hollow barrel connected to said chamber outlet;
   (c) an ejector operatively associated with said barrel;
   (d) a hollow needle connected to said body, with said hollow needle in fluid communication with said chamber through said inlet, so that blood can be rapidly drawn into said chamber through said needle, said needle is removed from said body using said hub member, and then blood dispensed by activating said ejector, wherein a chelating agent or anticoagulant is contained in said chamber and/or said needle in a predetermined amount; and
   (e) a hub member, with both said hollow needle and said body connected to said hub member, and with at least one of said hollow needle and said body removably connected to said hub member.

2. The apparatus of claim 1, wherein the body comprises a capillary body and the chamber comprises a capillary chamber, wherein the capillary chamber is sized and configured such that blood is rapidly drawn into said capillary chamber through said needle by capillary action.

3. The apparatus of claim 1, wherein the chamber is configured to draw blood therein by pressure from the blood vessel.

4. The apparatus of claim 1, wherein said ejector comprises a compressible bulb configured to dispense blood by compressing said bulb.

5. The apparatus of claim 4, wherein said compressible bulb is further configured to draw blood into said chamber through said needle by movement from a compressed position to an expanded position thereby creating negative pressure in said chamber.

6. The apparatus of claim 1, wherein said ejector comprises a plunger.

7. The apparatus of claim 1, further comprising a vent opening formed in either said barrel or said ejector, with said chamber in fluid communication with said vent opening.

8. The apparatus of claim 7, wherein said plunger has a blunt end portion configured for depression of said plunger into said barrel, and wherein said vent opening is formed in said blunt end portion.

9. The apparatus of claim 1, wherein said barrel has at least one laterally projecting grasping projection connected thereto.

10. The apparatus of claim 1, wherein said chamber, said barrel, said ejector, and said needle are all axially aligned with one another.

11. The apparatus of claim 1, wherein said chelating agent or anticoagulant is in dry powder form comprising a salt of ethylenediaminetetraacetic acid (EDTA).

12. The apparatus of claim 1, wherein said chelating agent or anticoagulant comprises droplets.

13. The apparatus of claim 1, further comprising a liquid or gel reagent composition in said chamber in a predetermined amount.

14. The apparatus of claim 8, further comprising a one-way valve positioned on the plunger adjacent a side of said capillary chamber having the vent opening thereon and upstream from the barrel chamber, wherein blood is permitted by the one-way valve to be dispensed into a device via said inlet by actuating said plunger.

15. The apparatus of claim 1, wherein at least a portion of said body is transparent, said body further comprising a porous indicator element positioned in said chamber outlet opening adjacent a transparent portion of said body.

16. The apparatus of claim 1, wherein said capillary chamber has a volume of from 2 to 200 microliters.

17. The apparatus of claim 1, wherein said hollow needle has a length of from 5 to 50 millimeters.

18. The apparatus of claim 1, wherein said hollow needle is between 14 to 25 gauge.

19. The apparatus of claim 1, wherein said hollow needle has at least one lateral vent opening formed therein and configured to facilitate rapid blood collection.

20. The apparatus of claim 1, wherein said body and said hollow needle are removably connected to one another through linear frictional engagement, optionally through said hub member.

21. The apparatus of claim 20, wherein said hub member comprises at least one laterally projecting grasping member connected thereto.

22. A method of collecting a blood sample from a subject with a blood collecting apparatus comprising: a body having a chamber formed therein, said chamber having an inlet and outlet, with said chamber configured to draw blood therein; a hollow barrel connected to said chamber outlet; an ejector operatively associated with said barrel; a hollow needle connected to said body, with said hollow needle in fluid communication with said chamber through said inlet, and a hub member, with both said hollow needle and said body connected to said hub member, and with at least one of said hollow needle and said body removably connected to said hub member, the method comprising:

(a) inserting the hollow needle of the apparatus into said subject for a time sufficient for said chamber to at least partially fill with said blood sample;
(b) withdrawing said needle from the subject;
(c) separating said needle from said chamber using said hub member; and then
(d) dispensing said blood sample from said chamber by actuating said ejector; wherein a chelating agent or anticoagulant is contained in said chamber and/or said needle in a predetermined amount.

23. The method of claim 22, wherein said subject is a bovine.

24. The method of claim 22, wherein said needle is inserted into a blood vessel of the subject.

25. The method of claim 22, wherein steps (a) through (d) are carried out in a time of one minute or less.

* * * * *